| United States Patent [19] | [11] Patent Number: 4,587,331 |
| Hlavka et al. | [45] Date of Patent: May 6, 1986 |

[54] PLATINUM COMPLEXES OF POLYHYDROXYLATED ALKYLAMINES AND 2-POLYHYDROXYLATED ALKYL-1,2-DIAMINOETHANES

[75] Inventors: Joseph J. Hlavka, Tuxedo; Ralph G. Child, Pearl River; Panayota Bitha, Pomona; Yang I. Lin, Nanuet, all of N.Y.

[73] Assignee: American Cyanamid Company, Stamford, Conn.

[21] Appl. No.: 682,883

[22] Filed: Dec. 17, 1984

[51] Int. Cl.[4] ........................ C07H 17/00; C07F 15/00
[52] U.S. Cl. ........................................ 536/55; 536/18.7; 536/121; 536/22; 556/137
[58] Field of Search ................... 536/55, 121, 22, 18.7; 260/429 R; 556/137

[56] References Cited

U.S. PATENT DOCUMENTS 4,200,583  4/1980  Kidani et al. .................... 536/55
4,203,912  5/1980  Hydes et al. .................... 260/429 R
4,225,529  9/1980  Hydes et al. .................... 260/429 R

FOREIGN PATENT DOCUMENTS 0103192  8/1981  Japan ............................... 536/55

*Primary Examiner*—Johnnie R. Brown
*Attorney, Agent, or Firm*—Edward A. Conroy, Jr.

[57] ABSTRACT

Platinum complexes of polyhydroxylated alkylamines and 2-polyhydroxylated alkyl-1,2-diaminoethanes useful for inducing regression and/or palliation of cancer diseases in mammals.

25 Claims, No Drawings

PLATINUM COMPLEXES OF POLYHYDROXYLATED ALKYLAMINES AND 2-POLYHYDROXYLATED ALKYL-1,2-DIAMINOETHANES

SUMMARY OF THE INVENTION

This invention relates to platinum complexes of organic compounds. Some of these compounds occur in both linear and cyclic form and may be represented by either formula (1) or formula (2):

$$\text{Formula (1)} \quad \text{Formula (2): } R_5-(CHOH)_n-R_6 \cdot A$$

wherein, in formula (1), $R_1$ is selected from the group consisting of hydrogen, alkyl ($C_1$–$C_3$), hydroxymethyl and aminomethyl; and $R_2$, $R_3$ and $R_4$ are each individually selected from the group consisting of hydroxy and amino with the proviso that at least one of $R_2$, $R_3$ and $R_4$ must be hydroxy; and wherein, in formula (2), $R_5$ is selected from the group consisting of $$-\underset{NH_2}{\underset{|}{CH}}\text{—CHO}, \quad -CH=NH, \quad -CH_2NH_2, \quad -\underset{NH_2}{\underset{|}{CH}}CHCHO,$$

$$-\underset{NH_2}{\underset{|}{CH}}CH_2NH_2, \quad -\underset{NH_2}{\underset{|}{CH}}COOH, \quad -CHO, \quad -\underset{NH_2}{\underset{|}{CH}}CH=NH,$$

$$-\underset{NH_2}{\underset{|}{CH}}CH=NNH_2, \quad -CH=NNH_2 \text{ and } -CH_2NHNH_2$$

and n is an integer 2–4 and $R_6$ is selected from the group consisting of methyl, hydroxymethyl and aminomethyl; and wherein in both formulae (1) and (2), A is selected from the group consisting of $$\underset{L'}{\overset{L}{Pt}} \quad \text{and} \quad \underset{L'}{\overset{OH}{Pt}}\overset{L}{\underset{OH}{}}$$

wherein L and L' are the same or different and are each selected from the group consisting of halide, nitrate, sulfate and a monobasic organic acid such as glucuronic acid, or L and L' taken together may be a dibasic organic acid such as malonic acid, oxalic acid methylmalonic acid, succinic acid, tartronic acid or 1,1-cyclobutane dicarboxylic acid.

Non-complexed compounds which occur in either linear or cyclic form include the following:
2-amino-2-deoxy-βD-glucopyranose
α-D-lyxopyranosylamine
D-mannopryanosylamine
2,3-diamino-2,3-dideoxy-α-D-glucopyranose
D-ribopyranosylamine
D-galactopyranosylamine
D-arabinopyranosylamine
6-amino-6-deoxy-α-D-glucopyranose
2,6-diamino-2,6-dideoxy-α-D-glucopyranose
2-amino-2-deoxy-D-glucopyranosylamine
D-xylopyranosylamine
2,3-diamino-2,3-dideoxy-D-glucopyranose.

Non-complexed compounds which occur only in the linear form represented by formula (2) include the following:
1,2-diamino-1,2-dideoxy-D-glucitol
2-amino-2-deoxy-D-gluconic acid
1,2-diamino-1,2-dideoxy-D-mannitol
2-amino-2-deoxy-D-glucose
L-arabinose hydrazone
D-galactose hydrazone.

In addition this invention is concerned with the compound 2-deoxy-D-streptamine, compound with platinum bromide chloride (1:1) which has the formula:

DETAILED DESCRIPTION OF THE INVENTION

The compounds of this invention may be prepared by treating the uncomplexed sugars with potassium tetrachloroplatinate in an aqueous medium for several hours.

The novel complexed compounds of this invention possess the property of inhibiting the growth of transplanted tumors in mammals as established by the following tests.

Lymphocytic Leukemia P388 Test

The animals used were BDF/1 mice, all of one sex, weighing a minimum of 18 g and all within a 3 g weight range. There were 5 or 6 animals per test group. The tumor transplant was by intraperitoneal injection of 0.5 ml of dilute ascitic fluid containing $10^6$ cells of lymphocytic leukemia P388. The test compounds were administered intraperitoneally on days 1, 5 and 9 relative to tumor inoculation, at various doses. The animals were weighed and the survivors recorded on a regular basis for 30 days. The median survival time and the ratio of survival time for treated (T)/control (C) animals were calculated. The positive control compound was either Cisplatin or 1,4-dihydroxy-5,8-bis[[2-(2-hydroxyethylamino)ethyl]amino]anthraquinone, dihydrochloride (U.S. Pat. No. 4,197,249). The results of this test with representative compounds of this invention appear in Table I.

TABLE I

| Lymphocytic Leukemia P388 Test | | | |
|---|---|---|---|
| Compound | Dose (mg/kg) | Median Survival (Days) | T/C × 100 (%) |
| 2-Amino-2-deoxy-β-D-gluco- | 50 | 17 | 173 |
| pyranose, compound with | 12 | 15.5 | 158 |
| platinum chloride (1:1) | 3 | 10.5 | 107 |
| Control | — | 9.8 | — |
| Cisplatin | 2 | 27.5 | 280 |
| | 1 | 22 | 227 |
| | 0.5 | 20 | 204 |
| | 0.25 | 17 | 173 |
| α-D-Lyxopyranosylamine, | 50 | 26.5 | 260 |
| compound with platinum | 25 | 24.5 | 240 |

TABLE I-continued
Lymphocytic Leukemia P388 Test

| Compound | Dose (mg/kg) | Median Survival (Days) | T/C × 100 (%) |
|---|---|---|---|
| chloride (1:1) | 12 | 23.5 | 230 |
|  | 6 | 21.5 | 211 |
|  | 3 | 20 | 196 |
| Control | — | 10.2 | — |
| Cisplatin | 1 | 24.5 | 240 |
|  | 0.5 | 23 | 225 |
|  | 0.25 | 19.5 | 191 |
|  | 0.125 | 17.5 | 172 |
| D-Mannopyranosylamine, compound with platinum chloride (1:1) | 100 | 15 | 140 |
|  | 50 | 14.5 | 136 |
|  | 25 | 13.5 | 126 |
|  | 12 | 12 | 112 |
| Control | — | 10.7 | — |
| Cisplatin | 1 | 21 | 196 |
|  | 0.5 | 21.5 | 201 |
|  | 0.25 | 16 | 150 |
|  | 0.125 | 14.5 | 136 |
|  | 0.06 | 13.5 | 126 |
| 2-Deoxy-D-streptamine, compound with platinum bromide chloride (1:1) | 100 | 28.5 | 252 |
|  | 50 | 27 | 239 |
|  | 25 | 23 | 204 |
|  | 12 | 19 | 168 |
|  | 6 | 18.5 | 164 |
|  | 3 | 15 | 133 |
| Control | — | 11.3 | — |
| Cisplatin | 1.5 | >29 | >257 |
|  | 0.8 | 21.5 | 190 |
|  | 0.4 | 16.5 | 146 |
|  | 0.2 | 14 | 124 |
| 2,3-Diamino-2,3-dideoxy-α-D-glucopyranose, compound with platinum chloride (1:1) | 100 | 28 | 259 |
|  | 50 | 26.5 | 245 |
|  | 25 | 20.5 | 190 |
|  | 12 | 18 | 167 |
|  | 6 | 17 | 157 |
|  | 3 | 16 | 148 |
| Control | — | 10.8 | — |
| Cisplatin | 1 | 28.5 | 264 |
|  | 0.25 | 18.5 | 171 |
|  | 0.06 | 14.5 | 134 |
|  | 0.015 | 14 | 130 |
| 1,2-Diamino-1,2-dideoxy-D-glucitol, compound with platinum chloride (1:1) | 25 | 22.5 | 199 |
|  | 12 | 19 | 168 |
|  | 6 | 17 | 150 |
|  | 3 | 16 | 142 |
|  | 1.5 | 14 | 124 |
| Control (No intraperitoneal standard) | — | 11.3 | — |
| D-Ribopyranosylamine, compound with platinum chloride (1:1) | 25 | 27.5 | 243 |
|  | 12 | 23.5 | 208 |
|  | 6 | 21 | 186 |
|  | 3 | 17.5 | 155 |
|  | 1.5 | 14.5 | 128 |
| Control | — | 11.3 | — |
| Cisplatin | 1.6 | 24 | 212 |
|  | 0.4 | 19.5 | 172 |
|  | 0.1 | 14 | 124 |
|  | 0.025 | 13 | 115 |
| D-Galactopyranosylamine, compound with platinum chloride (1:1) | 50 | 28.5 | 252 |
|  | 25 | 27 | 239 |
|  | 12 | 24 | 212 |
|  | 6 | 18.5 | 164 |
|  | 3 | 19 | 168 |
|  | 1.5 | 15 | 133 |
| Control | — | 11.3 | — |
| Cisplatin | 1.6 | 24 | 212 |
|  | 0.4 | 19.5 | 172 |
|  | 0.1 | 14 | 124 |
|  | 0.025 | 13 | 115 |
| 2-Amino-2-deoxy-D-gluconic acid, compound with platinum chloride (1:1) | 100 | 15.5 | 132 |
|  | 50 | 13.5 | 115 |
|  | 12 | 15.5 | 132 |
| Control | — | 11.7 | — |
| Cisplatin | 1.0 | >30 | >256 |
|  | 0.25 | 17.5 | 150 |
|  | 0.06 | 14 | 120 |
|  | 0.015 | 12.5 | 107 |
| D-Arabinopyranosylamine, compound with platinum chloride (1:1) | 25 | 26.5 | 212 |
|  | 12 | 27.5 | 220 |
|  | 6 | 23 | 184 |
|  | 3 | 19 | 152 |
|  | 1.5 | 19 | 152 |
|  | 0.8 | 20 | 160 |
| Control | — | 12.5 | — |
| Cisplatin | 1 | 29 | 232 |
|  | 0.25 | 19.5 | 156 |
|  | 0.06 | 15 | 120 |
|  | 0.015 | 14 | 112 |
| 1,2-Diamino-1,2-dideoxy-D-glucitol, compound with platinum chloride (1:1) and 1,2-dideoxy-D-mannitol, compound with platinum chloride (1:1) | 25 | 22.5 | 201 |
|  | 12 | 18.5 | 165 |
|  | 6 | 15.5 | 138 |
|  | 3 | 12.5 | 112 |
| Control | — | 11.2 | — |
| Cisplatin | 1.6 | 23.5 | 210 |
|  | 0.4 | 15 | 134 |
|  | 0.1 | 19.5 | 174 |
|  | 0.025 | 13 | 116 |
| 1,2-Diamino-1,2-dideoxy-D-glucose, compound with dichlorodihydroxy platinum (1:1) | 50 | 28.5 | 252 |
|  | 25 | 21.5 | 190 |
|  | 12 | 19.5 | 173 |
|  | 6 | 17 | 150 |
| Control | — | 11.3 | — |
| Cisplatin | 1 | 22 | 195 |
|  | 0.25 | 17 | 150 |
|  | 0.06 | 14 | 124 |
|  | 0.015 | 13 | 115 |
| 6-Amino-6-deoxy-α-D-glucopyranose, compound with platinum chloride (1:1) | 100 | 20.5 | 158 |
|  | 50 | 17.5 | 135 |
|  | 25 | 16 | 123 |
|  | 12 | 14.5 | 112 |
| Control | — | 13 | — |
| Cisplatin | 1.0 | >30 | >231 |
|  | 0.25 | 18 | 138 |
|  | 0.06 | 16 | 123 |
|  | 0.015 | 14.5 | 112 |
| 2,6-Diamino-2,6-dideoxy-α-D-glucopyranose, compound with platinum chloride (1:1) | 100 | 18 | 138 |
|  | 50 | 14.5 | 112 |
| Control | — | 13 | — |
| Cisplatin | 1.0 | >30 | >231 |
|  | 0.25 | 18 | 138 |
|  | 0.06 | 16 | 123 |
|  | 0.015 | 14.5 | 112 |
| D-Xylopyranosylamine, compound with platinum chloride (1:1) | 100 | 25 | 234 |
|  | 50 | 27.5 | 257 |
|  | 25 | 26 | 243 |
|  | 12 | 21 | 196 |
|  | 6 | 17.5 | 164 |
|  | 3 | 16.5 | 154 |
| Control | — | 10.7 | — |
| 1,4-Dihydroxy-5,8-bis[[2-(2-hydroxyethylamino)ethyl]-amino]anthraquinone, dihydrochloride | 0.4 | 21.5 | 201 |
|  | 0.1 | 16 | 150 |
|  | 0.025 | 17 | 159 |
|  | 0.006 | 13 | 121 |
| 1,2-Diamino-1,2-dideoxy-D-glucitol, compound with [1,1-cyclobutanedicarboxylato(2-)]-platinum (1:1) | 100 | 20 | 190 |
|  | 50 | 16.5 | 157 |
|  | 25 | 15.5 | 148 |
|  | 12 | 14 | 133 |
|  | 6 | 13 | 124 |
| Control | — | 10.5 | — |
| Cisplatin | 1 | >30 | >286 |
|  | 0.25 | 18 | 171 |
|  | 0.06 | 16 | 152 |
|  | 0.015 | 14.5 | 138 |

Melanotic Melanoma B16

The animals used were C57BC/6 mice, all of the same sex, weighing a minimum of 17 g and all within a 3 g weight range. There were 10 animals per test group. A 1 g portion of melanotic melanoma $B_{16}$ tumor was homogenized in 10 ml of cold balanced salt solution and a 0.5 ml aliquot of the homogenate was implanted intraperitoneally into each of the test mice. The test compounds were administered intraperitoneally on days 1 through 9, relative to tumor inoculation, at various doses. The animals were weighed and survivors recorded on a regular basis for 60 days. The median survival time for treated (T)/control (C) animals were calculated. The positive control compound was Cisplatin. The results of this test appear in Table II.

TABLE II

Melanotic Melanoma $B_{16}$ Test

| Compound | Dose (mg/kg) | Median Survival (Days) | T/C × 100 (%) |
|---|---|---|---|
| 2,3-Diamino-2,3-dideoxy-α-D-glucopyranose, compound with platinum chloride (1:1) | 12 | 43.5 | 238 |
| | 6 | 25.5 | 139 |
| Control | — | 18.3 | — |
| Cisplatin | 0.4 | 37 | 202 |
| | 0.1 | 36 | 197 |
| | 0.025 | 29.5 | 162 |
| D-Ribopyranosylamine, compound with platinum chloride (1:1) | 6 | 32.5 | 146 |
| | 3 | 28 | 126 |
| | 1.5 | 27 | 122 |
| | 0.8 | 28 | 126 |
| Control | — | 22.2 | — |
| Cisplatin | 0.25 | 32 | 144 |
| | 0.06 | 29 | 131 |
| | 0.015 | 25 | 113 |
| D-Galactopyranosylamine, compound with platinum chloride (1:1) | 12 | 32.5 | 154 |
| | 6 | 27 | 129 |
| | 3 | 26 | 124 |
| | 1.5 | 26 | 124 |
| | 0.8 | 23.5 | 112 |
| Control | — | 21 | — |
| Cisplatin | 1.0 | 32.5 | 154 |
| | 0.25 | 26.5 | 126 |
| | 0.06 | 23 | 110 |
| | 0.015 | 21.5 | 102 |
| 1,2-Diamino-1,2-dideoxy-D-glucitol, compound with [1,1-cyclobutanedicarboxylato(2-)]-platinum (1:1) | 50 | 28 | 156 |
| | 25 | 27.5 | 153 |
| | 12 | 22.5 | 125 |
| | 6 | 20 | 111 |
| Control | — | 18 | — |
| Cisplatin | 1 | 32.5 | 181 |
| | 0.25 | 26.5 | 147 |
| | 0.06 | 23 | 128 |
| | 0.015 | 21.5 | 119 |

Colon 26 Adenocarcinoma Test

The animals used were Balb/C mice all of one sex, weighing a minimum of 17 g and all within a 3 g weight range. There were 5 or 6 mice per test group with three groups of 5 or 6 animals used as untreated controls for each test. The tumor implant was by intraperitoneal (or subcutaneous) injection of 0.5 ml of a 2% Colon 26 tumor brei in Eagle's MEM medium containing antibiotics. The test compounds were administered intraperitoneally on days 1, 5 and 9 (relative to tumor implant doses). The mice were weighed and deaths recorded on a regular basis for 30 days. The median survival times and the ratio of survival time for treated (T)/control (C) animals were calculated. The positive control compound was Cisplatin. The results of this test on representative compounds of this invention appear in Table III.

TABLE III

Colon 26 Adenocarcinoma Test

| Compound | Dose (mg/kg) | Median Survival (Days) | T/C × 100 % |
|---|---|---|---|
| α-D-Lyxopyranosylamine, compound with platinum chloride (1:1) | 25 | 46.5 | 147 |

TABLE III-continued

Colon 26 Adenocarcinoma Test

| Compound | Dose (mg/kg) | Median Survival (Days) | T/C × 100 % |
|---|---|---|---|
| Control | — | 29.7 | — |
| Cisplatin | 1 | 43.5 | 147 |
| 2-Deoxy-D-streptamine, compound with platinum bromide chloride (1:1) | 25 | >60 | >159 |
| Control | — | 37.7 | — |
| Cisplatin | 1 | >60 | >159 |
| | 0.5 | >60 | >159 |
| 2,3-Diamino-2,3-dideoxy-α-D-glucopyranose, compound with platinum chloride (1:1) | 50 | >60 | >382 |
| | 25 | 31 | 197 |
| | 12 | 25 | 159 |
| | 6 | 27 | 172 |
| Control | — | 15.7 | — |
| Cisplatin | 0.5 | >60 | >382 |
| 1,2-Diamino-1,2-dideoxy-D-glucitol, compound with platinum chloride (1:1) | 12 | 44 | 122 |
| | 6 | 42 | 117 |
| Control | — | 36 | — |
| Cisplatin | 1 | 58 | 161 |
| | 0.5 | 46 | 128 |
| D-Ribopyranosylamine, compound with platinum chloride (1:1) | 25 | 46 | 147 |
| | 12 | 46 | 147 |
| | 6 | 41 | 131 |
| Control | — | 31.3 | — |
| Cisplatin | 1.0 | 59 | 188 |
| | 0.5 | 59 | 188 |
| D-Galactopyranosylamine, compound with platinum chloride (1:1) | 12 | 46 | 147 |
| Control | — | 31.3 | — |
| Cisplatin | 1.0 | 59 | 188 |
| | 0.5 | 59 | 188 |
| 1,2-Diamino-1,2-dideoxy-D-glucitol, compound with [1,1-cyclobutanedicarboxylato-(2-)]-platinum (1:1) | 50 | 21 | 134 |
| | 25 | 21 | 134 |
| | 12 | 17 | 108 |
| Control | — | 15.7 | — |
| Cisplatin | 1.0 | 59 | 376 |
| | 0.5 | 59 | 376 |

Lymphocytic Leukemia L1210 Test

The animals used were $BDF_1$ or $CD_2F_1$ mice, all of one sex, weighing a minimum of 17 g and all within a 3 g weight range. There were 6 mice in each test group and 18 in control groups. The tumor transplant was by intraperitoneal injection of 0.5 ml of lymphocytic leukemia L1210 at a concentration of $10^5$ cells per mouse. The test compounds were administered on days 1, 5 and 9 (relative to tumor inoculation) at various doses. The mice were weighed and survivors recorded on a regular basis for 30 days. The median survival time and the ratio of survival time for treated (T)/control (C) animals were calculated. The positive control compounds were Cisplatin and 5-fluorouracil given intraperitoneally at the indicated doses. The results of this test on representative compounds of this invention appear in Table IV.

TABLE IV

Lymphocytic Leukemia L1210 Test

| Compound | Dose (mg/kg) | Median Survival (Days) | T/C × 100 % |
|---|---|---|---|
| α-D-Lyxopyranosylamine, compound with platinum chloride (1:1) | 100 | 15.4 | 183 |
| | 50 | 11.8 | 140 |
| | 25 | 9.8 | 117 |
| | 12.5 | 9.0 | 107 |
| Control | — | 8.4 | — |

TABLE IV-continued
Lymphocytic Leukemia L1210 Test

| Compound | Dose (mg/kg) | Median Survival (Days) | T/C × 100 % |
|---|---|---|---|
| Cisplatin | 12 | 11.2 | 133 |
|  | 6 | 22.6 | 269 |
|  | 3 | 17.6 | 210 |
|  | 1.5 | 10.0 | 119 |
| 5-Fluorouracil | 60 | 17.6 | 210 |
| 2,3-Diamino-2,3-dideoxy-α-D-glucopyranose, compound with platinum chloride (1:1) | 50 | 11.0 | 131 |
|  | 25 | 9.6 | 114 |
|  | 12.5 | 9.0 | 107 |
| Control | — | 8.4 | — |
| Cisplatin | 12 | 11.2 | 133 |
|  | 6 | 22.6 | 269 |
|  | 3 | 17.6 | 210 |
|  | 1.5 | 10.0 | 119 |
| 5-Fluorouracil | 60 | 17.6 | 210 |
| 1,2-Diamino-1,2-dideoxy-D-glucitol, compound with platinum chloride (1:1) | 100 | 9.2 | 124 |
|  | 50 | 10.4 | 141 |
|  | 25 | 9.2 | 124 |
|  | 12.5 | 9.4 | 127 |
| Control | — | 7.4 | — |
| Cisplatin | 12 | 10.8 | 146 |
|  | 6 | 18.6 | 251 |
|  | 3 | 14.0 | 189 |
| 5-Fluorouracil | 60 | 18.2 | 246 |
| D-Ribopyranosylamine, compound with platinum chloride (1:1) | 100 | 16.6 | 180 |
|  | 50 | 12.4 | 135 |
|  | 25 | 11.4 | 124 |
|  | 12.5 | 10.2 | 111 |
| Control | — | 9.2 | — |
| Cisplatin | 12 | 9.2 | 100 |
|  | 6 | 20 | 217 |
|  | 3 | 17.4 | 189 |
| 5-Fluorouracil | 60 | 22.8 | 248 |
| D-Galactopyranosylamine, compound with platinum chloride (1:1) | 100 | 21 | 228 |
|  | 50 | 14.6 | 159 |
|  | 25 | 11.2 | 122 |
|  | 12.5 | 10.4 | 113 |
| Control | — | 9.2 | — |
| Cisplatin | 12 | 9.2 | 100 |
|  | 6 | 20 | 217 |
|  | 3 | 17.4 | 189 |
| 5-Fluorouracil | 60 | 22.8 | 248 |
| D-Arabinopyranosylamine, compound with platinum chloride (1:1) | 100 | 19.8 | 215 |
|  | 50 | 14.2 | 154 |
|  | 25 | 12.2 | 133 |
|  | 12.5 | 10.2 | 111 |
| Control | — | 9.2 | — |
| Cisplatin | 12 | 9.2 | 100 |
|  | 6 | 20 | 217 |
|  | 3 | 17.4 | 189 |
| 5-Fluorouracil | 60 | 22.8 | 248 |
| 1,2-Diamino-1,2-dideoxy-D-glucose, compound with dichlorodihydroxyplatinum (1:1) | 100 | 10 | 122 |
|  | 50 | 10 | 122 |
|  | 25 | 8.8 | 107 |
| Control | — | 8.2 | — |
| Cisplatin | 6 | 12.2 | 149 |
|  | 3 | 16.6 | 202 |
|  | 1.5 | 11.8 | 144 |
| 5-Fluorouracil | 60 | 20.2 | 246 |
| 6-Amino-6-deoxy-α-D-glucopyranose, compound with platinum compound (1:1) | 100 | 10 | 107 |
|  | 25 | 9.6 | 103 |
| Control | — | 9.3 | — |
| Cisplatin | 12 | 12.8 | 138 |
|  | 6 | 12.8 | 200 |
|  | 3 | 13.2 | 142 |
| 5-Fluorouracil | 60 | 20.2 | 219 |
| D-Xylopyranosylamine, compound with platinum chloride (1:1) | 100 | 13.2 | 161 |
|  | 50 | 10.6 | 129 |
|  | 25 | 9.6 | 117 |
| Control | — | 8.2 | — |
| Cisplatin | 6 | 12.2 | 149 |
|  | 3 | 16.6 | 202 |
|  | 1.5 | 11.8 | 144 |
| 5-Fluorouracil | 60 | 20.2 | 246 |
| 1,2-Diamino-1,2-dideoxy-D-glucitol, compound with [1,1-cyclobutanedicarboxylato(2-)]-platinum (1:1) | 50 | 10.6 | 113 |
| Control | — | 9.4 | — |
| Cisplatin | 6 | 13.8 | 147 |
|  | 3 | 14.6 | 155 |
|  | 1.5 | 12.4 | 132 |
| 5-Fluorouracil | 60 | 16.6 | 177 |

Cisplatin Resistant Lymphocytic Leukemia L1210/Cis DPP

The L1210/Cis DPP tumor is a subline of L1210 leukemia, resistant to Cisplatin and maintained as an ascites tumor in DBA/2 mice. The assay for antitumor activity was performed as described above for L1210. The results on representative compounds of this invention appear in Table V.

TABLE V
Cisplatin Resistant Lymphocytic Leukemia L1210/Cis DPP

| Compound | Dose (mg/kg) | Median Survival (Days) | T/C × 100 % |
|---|---|---|---|
| α-D-Lyxopyranosylamine, compound with platinum chloride (1:1) | 100 | 8.6 | 116 |
|  | 25 | 7.4 | 100 |
| Control | — | 7.4 | — |
| Cisplatin | 12 | 8.8 | 119 |
|  | 6 | 8.0 | 108 |
|  | 3 | 7.8 | 105 |
|  | 1.5 | 7.8 | 105 |
| 5-Fluorouracil | 60 | 20 | 270 |
| 2,3-Diamino-2,3-dideoxy-α-D-glucopyranose, compound with platinum chloride (1:1) | 100 | 7.6 | 103 |
|  | 50 | 8.8 | 119 |
|  | 25 | 8.2 | 111 |
|  | 12.5 | 8.0 | 108 |
| Control | — | 7.4 | — |
| Cisplatin | 12 | 8.8 | 119 |
|  | 6 | 8.0 | 108 |
|  | 3 | 7.8 | 105 |
|  | 1.5 | 7.8 | 105 |
| 5-Fluorouracil | 60 | 20 | 270 |
| 1,2-Diamino-1,2-dideoxy-D-glucitol, compound with platinum chloride (1:1) | 50 | 9 | 107 |
|  | 25 | 8.8 | 105 |
|  | 12.5 | 8.6 | 102 |
| Control | — | 8.4 | — |
| Cisplatin | 12 | 7.6 | 90 |
|  | 6 | 9.2 | 110 |
|  | 3 | 8.8 | 105 |
| 5-Fluorouracil | 60 | 20.6 | 245 |
| D-Ribopyranosylamine, compound with platinum chloride (1:1) | 100 | 8.6 | 110 |
|  | 50 | 7.6 | 97 |
|  | 25 | 7.6 | 97 |
|  | 12.5 | 7.4 | 95 |
| Control | — | 7.8 | — |
| Cisplatin | 12 | 9.8 | 125 |
|  | 6 | 9.2 | 117 |
|  | 3 | 8.4 | 108 |
| 5-Fluorouracil | 60 | 25.2 | 323 |
| D-Galactopyranosylamine, compound with platinum chloride (1:1) | 100 | 8.6 | 110 |
|  | 50 | 7.6 | 97 |
|  | 25 | 7.6 | 97 |
|  | 12.5 | 7.4 | 95 |
| Control | — | 7.8 | — |
| Cisplatin | 12 | 9.8 | 125 |
|  | 6 | 9.2 | 117 |
|  | 3 | 8.4 | 108 |
| 5-Fluorouracil | 60 | 25.2 | 323 |
| D-Arabinopyranosylamine, compound with platinum chloride (1:1) | 100 | 9 | 115 |
|  | 50 | 8 | 103 |
|  | 25 | 7.6 | 97 |
|  | 12.5 | 7.8 | 100 |
| Control | — | 7.8 | — |

TABLE V-continued

Cisplatin Resistant Lymphocytic Leukemia L1210/Cis DPP

| Compound | Dose (mg/kg) | Median Survival (Days) | T/C × 100 % |
|---|---|---|---|
| Cisplatin | 12 | 9.8 | 125 |
|  | 6 | 9.2 | 117 |
|  | 3 | 8.4 | 108 |
| 5-Fluorouracil | 60 | 25.2 | 323 |
| 1,2-Diamino-1,2-dideoxy-D-glucose, compound with dichlorodihydroxyplatinum (1:1) | 100 | 8.6 | 112 |
|  | 50 | 8.0 | 104 |
|  | 25 | 7.8 | 101 |
|  | 12.5 | 7.8 | 101 |
| Control | — | 7.7 | — |
| Cisplatin | 6 | 8.8 | 114 |
|  | 3 | 8.0 | 104 |
|  | 1.5 | 8.6 | 112 |
| 5-Fluorouracil | 60 | >20 | >260 |
| 6-Amino-6-deoxy-α-D-glucopyranose, compound with platinum chloride (1:1) | 100 | 8.4 | 106 |
|  | 50 | 7.6 | 96 |
|  | 25 | 8.0 | 101 |
|  | 12.5 | 7.8 | 99 |
| Control | — | 7.9 | — |
| Cisplatin | 12 | 8.6 | 109 |
|  | 6 | 8.6 | 109 |
|  | 3 | 8.8 | 111 |
| 5-Fluorouracil | 60 | 26 | 329 |
| 2,6-Diamino-2,6-dideoxy-α-D-glucopyranose, compound with platinum chloride (1:1) | 100 | 8.8 | 111 |
|  | 50 | 8.6 | 109 |
|  | 25 | 8.4 | 106 |
|  | 12.5 | 8.2 | 104 |
| Control | — | 7.9 | — |
| Cisplatin | 12 | 8.6 | 109 |
|  | 6 | 8.6 | 109 |
|  | 3 | 8.8 | 111 |
| 5-Fluorouracil | 60 | 26.0 | 329 |
| D-Xylopyranosylamine, compound with platinum chloride (1:1) | 100 | 8.8 | 114 |
|  | 50 | 8.2 | 106 |
|  | 25 | 8.0 | 104 |
|  | 12.5 | 8.0 | 104 |
| Control | — | 7.8 | — |
| Cisplatin | 6 | 8.8 | 114 |
|  | 3 | 8.0 | 104 |
|  | 1.5 | 8.6 | 112 |
| 5-Fluorouracil | 60 | >20 | >260 |
| 1,2-Diamino-1,2-dideoxy-D-glucitol, compound with [1,1-cyclobutanedicarboxylato(2-)]-platinum (1:1) | 100 | 9.0 | 103 |
|  | 50 | 9.2 | 106 |
|  | 25 | 9.0 | 103 |
|  | 12.5 | 8.8 | 101 |
| Control | — | 8.7 | — |
| Cisplatin | 6 | 9.0 | 103 |
|  | 3 | 9.0 | 103 |
|  | 1.5 | 8.8 | 101 |
| 5-Fluorouracil | 60 | 16.2 | 186 |

M5076 Sarcoma

The M5076 reticular cell Sarcoma is propagated as subcutaneous (sc) implants in C57B2/6 female mice. In the assays for antitumor activity, BDF$_1$ mice of either sex were inoculated intraperitoneally (ip) or sc with 0.5 ml of a 10% tumor brei. Test compounds were administered ip on days 1, 5, 9, 13 and 17 relative to tumor inoculation on day zero. In animals implanted with tumor ip, the median survival time in days was determined for each drug dose used on day 60 and the ratio of survival time for treated (T)/control (C) animals wre calculated. In animals implanted with tumor sc, tumor measurements in mm were made by means of a vernier caliper on day 22 relative to tumor implantation and tumor weights in mg estimated by the formula: (length×(width)$^2$)/2 with appropriate T/C values being calculated.

The results of this test on representative compounds of this invention appear in Table VI, compared to the results obtained with Cisplatin and Cytoxan.

TABLE VI

| | | M5076 Sarcoma | | | |
|---|---|---|---|---|---|
| | | IP | | SC | |
| Compound | Dose (mg/kg) | Median Survival (Days) | T/C × 100 (%) | Avg. Tumor Wt. (mg) | T/C × 100 (%) |
| α-D-Lyxopyranosylamine, compound with platinum chloride (1:1) | 100 | >60 | >261 | 0 | 0 |
|  | 50 | >60 | >261 | 0 | 0 |
|  | 25 | 53.5 | 232 | 801 | 38 |
|  | 12.5 | 36 | 156 | 1332 | 63 |
| Control | — | 23 | — | 212 | — |
| Cisplatin | 6 | 45.5 | 198 | 0 | 0 |
|  | 3 | >60 | >261 | 0 | 0 |
|  | 1.5 | 56 | 243 | 552 | 26 |
| Cytoxan | 40 | 51.5 | 224 | 0 | 0 |
| 1,2-Diamino-1,2-dideoxy-D-glucitol, compound with platinum chloride (1:1) | 50 | 26 | 127 | 135 | 8 |
|  | 25 | >60 | >293 | 190 | 11 |
|  | 12.5 | 48 | 234 | 569 | 32 |
|  | 6.2 | 39 | 190 | 1723 | 96 |
| Control | — | 20.5 | — | 1786 | — |
| Cisplatin | 6 | 20 | 98 | 0 | 0 |
|  | 3 | >60 | >293 | 4 | 0 |
|  | 1.5 | 54.5 | 266 | 433 | 24 |
| Cytoxan | 40 | 44.5 | 217 | 11 | 0 |
| 2,3-Daimino-2,3-diedeoxy-α-D-glucopyranose, compound with platinum chloride (1:1) | 50 | 47 | 204 | 0 | 0 |
|  | 25 | 45.5 | 198 | 168 | 8 |
|  | 12.5 | 32.5 | 141 | 879 | 41 |
| Control | — | 23 | — | 2121 | — |
| Cisplatin | 6 | 45.5 | 198 | 0 | 0 |
|  | 3 | >60 | >261 | 0 | 0 |
|  | 1.5 | 56 | 243 | 552 | 26 |
| Cytoxan | 40 | 51.5 | 224 | 0 | 0 |
| D-Ribopyranosylamine, compound with platinum chloride (1:1) | 50 | >60 | >261 | | |
|  | 25 | >60 | >261 | | |
|  | 12.5 | 41 | 178 | | |

TABLE VI-continued

| | | M5076 Sarcoma | | | |
|---|---|---|---|---|---|
| | | IP | | SC | |
| | | Median | | | |
| | Dose | Survival | T/C × 100 | Avg. Tumor | T/C × 100 |
| Compound | (mg/kg) | (Days) | (%) | Wt. (mg) | (%) |
| | 6.2 | 35 | 152 | | |
| Control | — | 23 | — | | |
| Cisplatin | 6 | >60 | >261 | | |
| | 3 | >60 | >261 | | |
| | 1.5 | 57.5 | 250 | | |
| Cytoxan | 40 | 51.5 | 224 | | |
| D-Galactopyranosylamine, | 50 | >60 | >261 | | |
| compound with platinum | 25 | >60 | >261 | | |
| chloride (1:1) | 12.5 | 52.5 | 228 | | |
| | 6.2 | 38.5 | 167 | | |
| Control | — | 23 | — | | |
| Cisplatin | 6 | >60 | >261 | | |
| | 3 | >60 | >261 | | |
| | 1.5 | 57.5 | 250 | | |
| Cytoxan | 40 | 51.5 | 224 | | |

Human Breast (MX-1) Tumor Xenograft

The human breast (MX-1) carcinoma is propagated as subcutaneous (sc) implants in athymic (Balb/c nude) mice. In assays for antitumor activity, athymic (Balb/c nude) male mice were implanted sc with four to five 2 mm² tumor fragments on day zero. Test compounds were administered intraperitoneally (ip) once every fourth day for a total of three injections starting when tumors were approximately 100 mg in size (staging day, usually 14 days after tumor implantation). Tumor measurements were made in mm by means of a Vernier caliper on days 12 and 16 relative to staging day and tumor weights in mg estimated from the formula (Length×(width)²)/2.

The difference (Δ) in mean tumor weight (mean final tumor weight minus mean initial tumor weight) was determined for each test group and the treated (T)/control (C) value expressed in percent. The results of this test on a representative compound of this invention appears in Table VII in comparison with Cisplatin.

TABLE VII

| | | Human Breast (MX-1) Tumor Xenograft | | | | | |
|---|---|---|---|---|---|---|---|
| | | Days Post Staging | | | | | |
| | | 12 | | | 16 | | |
| | Dose | Δ Tumor | T/C | Survivors | Δ Tumor | T/C | Survivors |
| Compound | (mg/kg) | Wt (mg) | % | Treated | Wt (mg) | % | Treated |
| α-D-Lyxopyranosyl- | 100 | 62 | 7 | 4/5 | 157 | 13 | 1/5 |
| amine, compound with | 50 | 562 | 68 | 5/5 | 840 | 70 | 5/5 |
| platinum chloride | 25 | 893 | 97 | 5/5 | 1517 | 126 | 5/5 |
| (1:1) | 12.5 | 1165 | 141 | 5/5 | 1775 | 147 | 5/5 |
| Control | — | 824 | — | 10/10 | 1207 | — | 10/10 |
| Cisplatin | 3 | 485 | 59 | 5/5 | 723 | 60 | 5/5 |
| | 1.5 | 1090 | 132 | 5/5 | 1585 | 131 | 3/5 |

This aspect of the invention includes novel compositions of matter and the method of inducing the regression and/or palliation of leukemia and related cancers in mammals using the novel compounds of this invention when administered in amounts ranging from about 1 mg to about 1.2 g per square meter of body surface area per day. The interrelationship of dosages for animals of various sizes and species and humans (based on mg/m² of surface area) is described by Freireich, E. J., et al., Quantitative Comparison of Toxicity of Anticancer Agents in Mouse, Rat, Hamster, Dog, Monkey and Man. Cancer Chemother. Rep., 50, No. 4, 219-244, May 1966. A preferred dosage regimen for optimum results would be from about 3 mg/m²/day to about 200 mg/m²/day, and such dosage units are employed that a total of from about 5 mg to about 360 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular or subcutaneous routes.

The active compounds may be administered parenterally. Solutions or dispersions of the active compound can be prepared in water, suitably mixed with a surfactant such as hydroxypropylcellulose. Dispersions can also be prepared in glycerol, liquid polyethylene glycols, and mixtures thereof in oils. Under ordinary conditions of storage and use these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol, liquid polyethylene glycol), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be obtained by the use in the compositions of agents which delay absorption, for example, aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subject to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administrated. Daily dosages up to about 5 or 10 days are often sufficient. It is also possible to dispense one daily dosage or one dose on alternate or less frequency days. As can be seen from the dosage regimens, the amount of principal active ingredient administered is a sufficient amount to aid regression and palliation of the leukemia or the like, in the absence of excessive deleterious side effects of a cytotoxic nature to the host harboring the cancer. As used herein, cancer disease means blood malignancies such as leukamia, as well as other solid and non-solid malignancies such as the melanocarcinomas, lung carcinomas and mammary tumors. By regression and palliation is meant arresting or retarding the growth of the tumor or other manifestation of the disease compared to the course of the distance in the absence of treatment.

This invention will be described in greater detail in conjunction with the following non-limiting specific examples.

EXAMPLE 1

2-Amino-2-deoxy-$\beta$-D-glucopyranose, compound with platinum chloride (1:1)

To a solution of 1.0 g of D-glucosamine hydrochloride in 25 ml of water was added 250 mg of sodium methoxide followed by a solution of 1.92 g of potassium tetrachloroplatinate in 25 ml of water. The resulting solution was stirred for 4 days, then evaporated to dryness in vacuo. The residue was triturated with 25 ml of methanol, filtered and the filtrate cooled in an ice bath. The resulting solid was removed by filtration and the methanol filtrate evaporated to dryness, giving 1.0 g of the desired product.

EXAMPLE 2

$\alpha$-D-Lyxopyranosylamine, compound with platinum chloride (1:1)

To a solution of 1.0 g of D-lyxosylamine in 30 ml of water was added a solution of 2.78 g of potassium tetrachloroplatinate in 30 ml of water. This solution was stirred for 6 days, then evaporated in dryness in vacuo. The residue was triturated with 200 ml of methanol and filtered. The filtrate was evaporated to 50 ml and then poured into 100 ml of ether, giving 1.8 g of the desired product.

EXAMPLE 3

D-Mannopyranosylamine, compound with platinum chloride (1:1)

To 1.0 g of D-mannosamine hydrochloride in 20 ml of water was added a solution of 252 mg of sodium methoxide in 10 ml of water. The resulting solution was added to a solution of 1.93 g of potassium tetrachloroplatinate in 25 ml of water. This solution was stirred for 3 days, then evaporated to dryness. The residue was triturated with 100 ml of methanol and filtered. The filtrate was evaporated, giving 1.5 g of the desired product.

EXAMPLE 4

2-Deoxy-D-streptamine, compound with platinum bromide chloride (1:1)

To a solution of 1.0 g of 2-deoxy-D-streptamine dihydrobromide in 10 ml of water was added 338 mg of sodium methoxide. This solution was then added to a solution of 1.28 g of potassium tetrachloroplatinate in 25 ml of water. The mixture was stirred for several hours, giving 450 mg of the desired product.

EXAMPLE 5

2,3-Diamino-2,3-dideoxy-α-D-glucopyranose, compound with platinum chloride (1:1)

To a solution of 1.0 g of 2,3-diamino-2,3-dideoxy-α-D-glucose dihydrochloride in 20 ml of water was added 0.43 g of sodium methoxide followed by a solution of 1.65 g of potassium tetrachloroplatinate in 50 ml of water. This mixture was stirred for 2 days, then filtered and the filtrate evaporated to dryness. The residue was triturated overnight with 100 ml of methanol, then filtered. The filtrate was evaporated to dryness, giving 0.8 g of the desired product.

EXAMPLE 6

1,2-Diamino-1,2-dideoxy-D-glucitol, compound with platinum chloride (1:1)

A solution of 20 g of glucosamine hydrochloride, 9.1 g of phenyl hydrazine, 20 ml of glacial acetic acid and 80 ml of water was heated on a steam bath for one hour, then cooled and filtered. The filtrate was hydrogenated with 10 mg of Raney-nickel catalyst at 50 psi for 18 hours. This mixture was filtered through diatomaceous earth. The filtrate was refrigerated for 48 hours, then extracted with five 50 ml portions of toluene. The extracted aqueous filtrate was then stirred with 0.5 g of activated charcoal and filtered through diatomaceous earth. This filtrate was adjusted to pH 4.5 with sodium bicarbonate. A 75 ml portion of this filtrate was added to a suspension of 19.3 g of potassium tetrachloroplatinate in 80 ml of water, stirred for 20 hours, then cooled at 4° C. for 3 hours and the resulting solid collected by filtration. This solid was recrystallized from 250 ml of boiling water, giving 1.2 g of the desired product as yellow crystals, mp 262°-264° C. (dec.).

EXAMPLE 7

D-Ribopyranosylamine, compound with platinum chloride (1:1)

To 100 ml of methanol was added 20 g of D-ribose and 0.5 g of ammonium chloride. This mixture was treated with anhydrous ammonia at 0° C. until a solution was obtained. This solution was stored at 0° C. for 13 days, then the solid was collected, giving 13 g of D-ribopyranosylamine.

To a solution of 8.35 g of potassium tetrachloroplatinate in 80 ml of water was added a solution of 3.0 g of D-ribopyranosylamine in 75 ml of water. This mixture was stirred for 3 days, then filtered and the filtrate evaporated in vacuo to 20 ml. The remainder was filtered, the filtrate evaporated to dryness and the residue triturated with 100 ml of methanol. Evaporation of the methanol gave 300 mg of the desired product.

EXAMPLE 8

D-Galactopyranosylamine, compound with platinum chloride (1:1)

To a solution of 1 g of 1-amino-1-deoxy-β-D-galactose in 30 ml of water was added a solution of 2.31 g of potassium tetrachloroplatinate in 30 ml of water. This solution was stirred overnight, then filtered and the filtrate evaporated in vacuo to dryness. The residue was triturated with 150 ml of methanol for 2 days, then filtered. The filtrate was evaporated in vacuo, giving 300 mg of the desired product.

EXAMPLE 9

2-Amino-2-deoxy-D-gluconic Acid, compound with platinum chloride (1:1)

To a solution of 2.8 g of glucosamic acid in 75 ml of water was added a solution of 2.8 g of potassium tetrachloroplatinate in 30 ml of water. This mixture was stirred for 6 days, then evaporated to dryness. The residue was triturated with 150 ml of methanol for 2 hours, then the methanol was evaporated, giving 250 mg of the desired product.

EXAMPLE 10

D-Arabinopyranosylamine, compound with platinum chloride (1:1)

To a mixture of 20 g of arabinose and 0.5 g of ammonium chloride in 100 ml of methanol at 0° C. was added ammonia until a solution was obtained. The solution was stirred at 0° C. for 13 days, then the solid was collected, giving 14 g of 1-amino-1-deoxy-D-arabinose.

To a solution of 1.5 g of 1-amino-1-deoxy-D-arabinose in 30 ml of water was added a solution of 2.78 g of potassium tetrachloroplatinate in 30 ml of water. This solution was allowed to stand for 6 days and then evaporated to dryness in vacuo. The residue was triturated with 150 ml of methanol for 2 days, then filtered. The filtrate was evaporated, giving 600 mg of the desired product.

EXAMPLE 11

1,2-Diamino-1,2-dideoxy-D-glucitol, compound with platinum chloride (1:1) and
1,2-Diamino-1,2-dideoxy-D-mannitol, compound with platinum chloride (1:1)

A mixture of 18 g of glucose, 900 ml of water, 22.73 ml of glacial acetic acid and 39.32 ml of phenyl hydrazine was heated on a steam bath for 2 hours, then cooled and the solid collected, washed with water and dried. This solid was recrystallized from 180 ml of 50% pyridine, giving 9.0 g of D-arabinohexose phenyl osazone.

A mixture of 3.5 g of D-arabinohexose phenyl osazone, 39 mg of Raney-nickel catalyst and 90 ml of 2N potassium hydroxide in ethanol was reacted as described by Wolfran and Minieri, J. Org. Chem., 30, 841 (1965), giving 2.67 g of the Schiff bases of 1,2-diamino-1,2-dideoxy-glucitol and 1,2-diamino-1,2-dideoxy-mannitol as a mixture of isomers.

A 1.94 g portion of this mixture of isomers was suspended in 10 ml of water. A 4.16 ml portion of 3N hydrochloric acid was added, the mixture was stirred for one hour and the oily layer removed by extraction with four portions of ether. The remaining aqueous layer was stirred with activated carbon and filtered through diatomaceous earth. The pH of the filtrate was adjusted to 5.0 by the addition of 1.06 g of sodium acetate, then 2.08 g of potassium tetrachloroplatinate was added, the mixture was stirred to solution and then allowed to stand 6 days. The mixture of crystals and gelatinous solid was collected by filtration, washed three times with ice water and dried. This solid was recrystallized from hot water, giving 310 mg of the desired products as a mixture.

EXAMPLE 12

1,2-Diamino-1,2-dideoxy-D-glucitol, compound with dichlorodihydroxyplatinum (1:1)

A 450 mg portion of 1,2-diamino-1,2-dideoxy-D-glucitol, compound with platinum chloride was dissolved with stirring in 65 ml of boiling water. This solution was treated dropwise with 1 ml of 30% hydrogen peroxide. After stirring for one hour the solution was concentrated to 50 ml, refrigerated at 4° C. for 48 hours and then concentrated to an oil. This oil was triturated with ethanol and the resulting solid washed three times with ethanol, twice with ether, dried and then recrystallized from a minimum amount of water giving 330 mg of the desired product as a pale yellow solid, mp 200°–202° C. (dec.).

EXAMPLE 13

6-Amino-6-deoxy-α-D-glucopyranose, compound with platinum chloride (1:1)

To a solution of 900 mg of 6-amino-6-deoxy-D-glucose hydrochloride in 10 ml of water and added 226 mg of sodium methoxide. This was added to a solution of 1.77 g of potassium tetrachloroplatinate in 30 ml of water. This solution was stirred for 3 days, then filtered and evaporated to dryness. The residue was triturated with 80 ml of methanol overnight, then filtered and the filtrate evaporated, giving 680 mg of the desired product.

EXAMPLE 14

2,6-Diamino-2,6-Dideoxy-α-D-glucopyranose, compound with platinum chloride (1:1)

To a solution of 939 mg of 2,6-diamino-2,6-dideoxy-D-glucose dihydrochloride in 10 ml of water was added 424 mg of sodium methoxide. This was added to a solution of 1.55 g of potassium tetrachloroplatinate in 30 ml of water. This mixture was stirred for 3 days, filtered and the filtrate taken to dryness. The residue was triturated with 80 ml of methanol, filtered and the filtrate evaporated, giving 600 mg of the desired product.

EXAMPLE 15

2-Amino-2-Deoxy-D-glucopyranosylamine, compound with platinum chloride (1:1)

To a solution of 2.561 g of potassium tetrachloroplatinate in 30 ml of water was added a solution of 1 g of 2-amino-2-deoxy-D-glucopyranosylamine in 20 ml of water. This mixture was stirred 4 days, then evaporated to dryness in vacuo. The residue was triturated with 100 ml of methanol overnight, then filtered and the filtrate evaporated to dryness, giving 1.0 g of the desired product.

EXAMPLE 16

D-Xylopyranosylamine, compound with platinum chloride (1:1)

To a solution of 1.021 g of D-xyloseamine in 25 ml of water was added a solution of 2.82 g of potassium tetrachloroplatinate in 25 ml of water. This mixture was stirred for 3 days, then evaporated to dryness in vacuo. The residue was triturated with 100 ml of methanol for 48 hours, filtered and the filtrate evaporated to dryness in vacuo, giving 1.5 g of the desired product.

EXAMPLE 17

1,2-Diamino-1,2-dideoxy-D-glucitol, compound with [1,1-cyclobutanedicarboxylato(2-)]platinum (1:1)

A solution of 20 g of glucosamine hydrochloride, 20 ml of glacial acetic acid, 80 ml of water and 9.1 ml of phenylhydrazine was heated on a steam bath for one hour, then cooled and filtered. The filtrate was hydrogenated in a Parr apparatus with Raney nickel catalyst until the uptake of hydrogen ceased. This mixture was then filtered, the filtrate was treated with activated charcoal and refiltered through diatomaceous earth, giving a green solution. A 6.31 ml portion of this green solution was treated with 0.24 g of sodium bicarbonate and a suspension of 1.66 g of potassium tetrachloroplatinate in 8 ml of water. The resulting reddish brown solution was stirred overnight, then cooled to 4° C. for 3 hours and the resulting solid collected. A 100 mg portion of this solid was stirred with 15 ml of hot water and then filtered through diatomaceous earth. The filtrate was cooled giving a solid which was collected, giving 90 mg of 1,2-diamino-1,2-dideoxy-D-glucitol, compound with platinum chloride (1:1) as yellow grains, mp 265° C. (dec.).

A 1.0 g portion of 1,2-diamino-1,2-dideoxy-D-glucitol, compound with platinum chloride (1:1) (prepared as described above) was suspended in 5 ml of water and treated with 0.76 g of silver nitrate in 5 ml of water. This mixture was stirred for one hour and then filtered. The colorless filtrate was treated with a solution of 321 mg of 1,1-cyclobutane dicarboxylic acid in 4.5 ml of 1N sodium hydroxide and 5 ml of water. The resulting solution was allowed to stand overnight, then clarified through diatomaceous earth, treated with 7 volumes of 2-propanol and cooled for 48 hours. The resulting gummy precipitate was collected, washed and dried, giving 150 mg of the desired product as a colorless solid, mp 180°–185° C.

EXAMPLE 18

2-Amino-2-deoxy-D-glucose hydrazone, compound with platinum chloride (1:1)

A mixture of 2.0 g of glucosamine hydrochloride, 5 ml of methanol and 5 ml of hydrazine hydrate was stirred overnight and then evaporated to dryness giving 2-amino-2-deoxy-D-glucose hydrazone.

To a solution of 3.01 g of potassium tetrachloroplatinate in 33 ml of water was added a solution of 1.4 g of 2-amino-2-deoxy-D-glucose hydrazone in 20 ml of water. This mixture was allowed to stand for a few minutes then filtered. The filtrate was stirred overnight, then refiltered. This filtrate was evaporated to about 10 ml and refiltered. This filtrate was cooled in an ice bath, then refiltered. This filtrate was evaporated to dryness and the residue triturated with 40 ml of methanol, then filtered. The methanol filtrate was evaporated to about 10 ml and refiltered. This filtrate was evaporated to dryness, giving 900 mg of the desired product.

EXAMPLE 19

L-Arabinose hydrazone, compound with platinum chloride (1:1)

A solution of 2.0 g of L-arabinose in 5 ml of methanol and 5 ml of hydrazine hydrate was stirred overnight and then evaporated in vacuo. A 5 ml portion of methanol was added to the residue. After standing overnight the oil solidified. The solid was collected and dried, giving 1.5 g of L-arabinose hydrazone.

To a solution of 1.9 g of potassium tetrachloroplatinate in 20 ml of water was added a solution of 750 mg of L-arabinose hydrazone in 15 ml of water. This mixture was stirred for 15 minutes and then filtered. This filtrate was stirred overnight and then refiltered. This filtrate was evaporated in vacuo to about 15 ml and then filtered. This filtrate was evaporated to dryness and the residue triturated with 50 ml of methanol overnight, then filtered. This filtrate was evaporated to dryness, giving 450 mg of the desired product.

EXAMPLE 20

D-Galactose hydrazone, compound with platinum chloride (1:1)

A 2.0 g portion of D-galactose was dissolved in a mixture of 5 ml of methanol and 5 ml of hydrazine hydrate and stirred overnight, then evaporated to dryness in vacuo. About 5 ml of methanol was added, the mixture was stirred for 48 hours and the solid was collected giving 1.9 g of D-galactose hydrazone.

To a solution of 2.14 g of potassium tetrachloroplatinate in 20 ml of water was added a solution of 1.3 g of D-galactose hydrazone in 30 ml of water. After standing 30 minutes the mixture was filtered. This filtrate was stirred overnight and then refiltered. This filtrate was evaporated to dryness and the residue was triturated with 50 ml of methanol, then filtered. This filtrate was evaporated to about 25 ml and filtered. This filtrate was evaporated to about 10 ml and filtered. This filtrate was evaporated to dryness giving 960 mg of the desired product.

EXAMPLE 21

6-Deoxy-L-galactose hydrazone, compound with platinum chloride (1:1)

A solution of 4.0 g of 6-deoxy-L-galactose in 10 ml of methanol and 10 ml of hydrazine hydrate was stirred overnight, then evaporated to dryness, giving 4.4 g of 6-deoxy-L-galactose hydrazone.

To a solution of 2.33 g of potassium tetrachloroplatinate in 30 ml of water was added a solution of 1.0 g of 6-deoxy-L-galactose hydrazone in 20 ml of water. This mixture was filtered, the filtrate allowed to stand overnight and then evaporated to dryness. The residue was triturated with 50 ml of methanol overnight, then filtered and the filtrate evaporated to dryness, giving 1.4 g of the desired product.

EXAMPLE 22

D-Arabinose hydrazone, compound with platinum chloride (1:1)

A solution of 4.0 g of D-arabinose in 10 ml of methanol and 10 ml of hydrazine hydrate was stirred overnight, then evaporated to dryness in vacuo. The residue was triturated with 25 ml of methanol and the solid was collected, giving 3.5 g of D-arabinose hydrazone.

To a solution of 2.53 g of potassium tetrachloroplatinate in 30 ml of water was added 1.5 g of D-arabinose hydrazone. This solution was stirred for 2 hours, filtered and the filtrate stirred overnight, then refiltered. This filtrate was evaporated in vacuo to 10 ml and refiltered. This filtrate was evaporated to dryness, the residue triturated overnight with 70 ml of methanol, then filtered. This filtrate was evaporated to dryness, giving 510 mg of the desired product.

EXAMPLE 23

1-Deoxy-1-hydrazino-D-arabinitol, compound with platinum chloride (1:1)

A 1.5 portion of D-arabinose hydrazone in 40 ml of ethanol and 20 ml of water was reduced with 200 mg of platinum oxide and hydrogen for 4 hours. The mixture was then filtered and the filtrate evaporated to dryness. The residue was dissolved in 40 ml of methanol and then evaporated to dryness, giving 1.24 g of 1-deoxy-1-hydrazino-D-arabinitol.

To a 1.24 g of 1-deoxy-1-hydrazino-D-arabinitol in 20 ml of water was added a solution of 3.099 g of potassium tetrachloroplatinate in 50 ml of water. This mixture was stirred overnight, then evaporated to dryness in vacuo. The residue was triturated with 100 ml of methanol and then filtered. This filtrate was evaporated to dryness, giving 400 mg of the desired product.

EXAMPLE 24

2,3-Diamino-2,3-dideoxy-D-glucopyranose, compound with [1,1-cyclobutanedicarboxylato(2-)0,0']platinum To a solution of 500 mg of 2,3-diamino-2,3-dideoxy-D-glucose platinum chloride in 75 ml of water was added 405 mg of the disilver salt of 1,1-cyclobutanedicarboxylic acid. This mixture was stirred overnight, then filtered and the filtrate evaporated to dryness in vacuo, giving 500 mg of the desired product.

We claim:

1. A compound in linear or cyclic form selected from those of the formulae:

$$\begin{matrix} R_1 \\ \diagdown O \\ HO \diagup \diagdown R_4 \cdot A \\ \diagup \diagdown \\ R_2 \quad R_3 \end{matrix} \qquad R_5-(CHOH)_n-R_6 \cdot A$$

(1)      (2)

wherein in cyclic form (1) $R_1$ is selected from the group consisting of hydrogen, alkyl ($C_1$–$C_3$), hydroxymethyl and aminomethyl; and $R_2$, $R_3$ and $R_4$ are each individually selected from the group consisting of hydroxy and amino with the proviso that at least one of $R_2$, $R_3$ and $R_4$ must be hydroxy; and wherein in linear form (2) $R_5$ is selected from the group consisting of $$-\underset{\underset{NH_2}{|}}{\overset{\overset{CHO}{|}}{CH}}, \quad -CH=NH, \quad -CH_2NH_2, \quad -\underset{\underset{NH_2}{|}}{\overset{\overset{NH_2}{|}}{CH}}CHCHO,$$

$$-\underset{}{\overset{\overset{NH_2}{|}}{CH}}CH_2NH_2, \quad -\underset{}{\overset{\overset{NH_2}{|}}{CH}}COOH, \quad -CHO, \quad -\underset{}{\overset{\overset{NH_2}{|}}{CH}}CH=NH,$$

$$-\underset{}{\overset{\overset{NH_2}{|}}{CH}}CH=NNH_2, \quad -CH=NNH_2 \text{ and } -CH_2NHNH_2$$

and n is an integer 2–4 and $R_6$ is selected from the group consisting of methyl, hydroxymethyl and aminomethyl; and wherein in both cyclic (1) and linear form (2), A is selected from the group consisting of

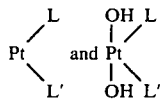

wherein L and L' are the same or different and are each selected from the group consisting of halide, nitrate and sulfate and L and L' taken together is selected from the group consisting of oxalic, malonic, methylmalonic, succinic, tartronic and 1,1-cyclobutanedicarboxylic acids.

2. The compound according to claim 1, 2-amino-2-deoxy-β-D-glucopyranose platinum chloride.

3. The compound according to claim 1, α-D-lyxopyranosylamine platinum chloride.

4. The compound according to claim 1, D-mannopyranosylamine platinum chloride.

5. The compound according to claim 1, 2,3-diamino-2,3-dideoxy-α-D-glucopyranose platinum chloride.

6. The compound according to claim 1, 1,2-diamino-1,2-dideoxy-D-glucitol platinum chloride.

7. The compound according to claim 1, D-ribopyranosylamine platinum chloride.

8. The compound according to claim 1, D-galactopyranosylamine platinum chloride.

9. The compound according to claim 1, 2-amino-2-deoxy-D-gluconic acid platinum chloride.

10. The compound according to claim 1, D-arabinopyranosylamine platinum chloride.

11. The compound according to claim 1, 1,2-diamino-1,2-dideoxy-D-mannitol platinum chloride.

12. The compound according to claim 1, 1,2-diamino-1,2-dideoxy-D-glucose dichlorodihydroxy platinum.

13. The compound according to claim 1, 6-amino-6-deoxy-α-D-glucopyranose platinum chloride.

14. The compound according to claim 1, 2,6-diamino-2,6-dideoxy-α-D-glucopyranose, platinum chloride.

15. The compound according to claim 1, 2-amino-2-deoxy-D-glucopyranosylamine platinum chloride.

16. The compound according to claim 1, D-xylopyranosylamine platinum chloride.

17. The compound according to claim 1, 1,2-diamino-1,2-dideoxy-D-glucitol[1,1-cyclobutanedicarboxylato(2-)]platinum.

18. The compound according to claim 1, 2-amino-2-deoxy-D-glucose hydrazone platinum chloride.

19. The compound according to claim 1, L-arabinose hydrazone platinum chloride.

20. The compound according to claim 1, D-galactose hydrazone platinum chloride.

21. The compound according to claim 1, 6-deoxy-L-galactose hydrazone platinum chloride.

22. The compound according to claim 1, D-arabinose hydrazone platinum chloride.

23. The compound according to claim 1, 1-deoxy-1-hydrazino-D-arabinitol platinum chloride.

24. The compound according to claim 1, 2,3-diamino-2,3-dideoxy-D-glucopyranose[1,1-cyclobutanedicarboxylato(2-)-0,0']platinum.

25. The compound 2-deoxy-D-streptamine platinum bromide chloride.

* * * * *